(12) United States Patent
Boettcher et al.

(10) Patent No.: US 6,333,339 B1
(45) Date of Patent: Dec. 25, 2001

(54) 3-BENZYLPIPERIDINE

(75) Inventors: Henning Boettcher, Darmstadt; Helmut Pruecher, Heppenheim; Hartmut Greiner, Weiterstadt; Christoph Seyfried, Seehein-Jugenheim; Andrew Barber, Weiterstadt, all of (DE); Joseph Maria Martinez, Barcelona (ES)

(73) Assignee: Merck Patent Gellschaft mit Beschrankter, Darmstadt (DE)

( * ) Notice: Subject to any disclaimer, the term of this patent is extended or adjusted under 35 U.S.C. 154(b) by 0 days.

(21) Appl. No.: 09/445,587

(22) PCT Filed: Jun. 8, 1998

(86) PCT No.: PCT/EP98/03429

§ 371 Date: Apr. 17, 2000

§ 102(e) Date: Apr. 17, 2000

(87) PCT Pub. No.: WO98/57953

PCT Pub. Date: Dec. 23, 1998

(30) Foreign Application Priority Data

Jun. 18, 1997 (DE) .............................. 197 25 664

(51) Int. Cl.⁷ ..................... A61K 31/445; C07D 401/06
(52) U.S. Cl. ............................. 514/323; 546/201
(58) Field of Search .............................. 514/323; 546/201

(56) References Cited

U.S. PATENT DOCUMENTS 4,251,538  2/1981  Hans-Heinrich et al. ........... 546/201
5,116,846  5/1992  Gary et al. ........................... 514/317
5,256,673  10/1993  Bottcher et al. ..................... 514/338

FOREIGN PATENT DOCUMENTS

| 0 518 805 | 12/1992 | (EP) . |
| 9424105 | 10/1994 | (WO) . |
| 9502592 | 1/1995 | (WO) . |
| 9533743 | 12/1995 | (WO) . |
| wo-98/28292 * | 7/1998 | (WO) . |

* cited by examiner

*Primary Examiner*—Ceila Chang
(74) *Attorney, Agent, or Firm*—Millen, White, Zelano & Branigan

(57) ABSTRACT

The invention relates to piperidine derivatives of the formula I

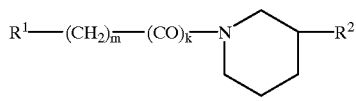

in which $R^1$, $R^2$, m and k have the meanings indicated in claim 1, and their salts, novel intermediates and processes for the preparation of the compounds according to the invention.

The compounds of the formula I are potent a receptor ligands and show 5-HT reuptake-inhibiting actions and can be used for the production of medicaments, for example for the treatment of disorders of the central nervous system, of strokes, brain or bone marrow traumata or of ischaemic states.

14 Claims, No Drawings

3-BENZYLPIPERIDINE

The invention relates to compounds of the formula I

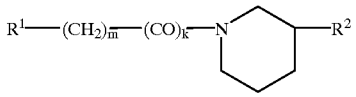

in which
R$^1$ is 2- or 3-indolyl which is unsubstituted or mono- or disubstituted by Hal, CN, A, AO, OH, CONH$_2$, CONHA, CONA$_2$, COOH and/or COOA, or is 5H-1,3-dioxolo-[4,5-f]-7-indolyl, R$^2$ is benzyl which is unsubstituted or mono-, di- or trisubstituted by A, AO, OH, Hal, CN, NO$_2$, NH$_2$, NHA, NA$_2$, CF$_3$, COA, CONH$_2$, COOH, CONHA, CONA$_2$, OSO$_2$A and/or OSO$_2$CF$_3$ or is phenylhydroxymethyl, Hal is F, Cl, Br or I, A is straight-chain or branched alkyl having 1–10 C atoms, which can be substituted by 1 to 5 F and/or Cl atoms or is cycloalkyl having 3–10 C atoms, k is 0 or 1 and m is 1, 2, 3 or 4 and their physiologically acceptable salts and solvates.

Compounds of similar structure are disclosed, for example, in the documents WO 95/02592 or WO 95/33743.

The invention is based on the object of finding novel compounds having useful properties, in particular those which can be used for the production of medicaments.

It has now been found that the compounds of the formula I and their salts have particularly useful pharmacological properties together with good tolerability. They exhibit actions on the central nervous system and have potent anti-epileptic and especially antiischaemic properties (this was shown in the model of transient occlusion of the middle cerebral artery in rats and reduction of the neurological scores). These substances are potent σ receptor ligands with neuroprotective properties (M. O'Neill et al., European J. Pharmacol. 283 (1995), 217–225). Compounds which act as σ receptor ligands also affect the NMDA ion channel complex (see also H. Yamamoto et al., J. Neuroscience (1995), 15(1), 731–736). σ Agonists additionally have a favourable effect on age-related memory disorders (cf. Maurice et al., Brain Research 733 (1996), 219–230). Some of the compounds of the formula I furthermore show a strong 5-HT reuptake-inhibiting action. For such compounds, a particularly good antidepressant, anxiolytic action, as well as a positive effect on obsessive-compulsive disorder (OCD), eating disorders such as bulimia, tardive dyskinesias, learning disorders, age-dependent memory disorders and psychoses are to be expected.

Compounds of the formula I and their physiologically acceptable acid addition salts have particularly useful pharmacological properties together with good tolerability. The compounds are suitable for the treatment of schizophrenia, cognitive deficits, anxiety, depression, nausea, tardive dyskinesia, gastrointestinal tract disorders or Parkinsonism. They exhibit actions on the central nervous system, especially 5-HT reuptake inhibiting actions. For the ex-vivo detection of serotonin reuptake inhibition, synaptosomal uptake inhibition (Wong et al., Neuropsychopharmacol. 8 (1993), 23–33 and p-chloroamphetamine antagonism (Fuller et al., J. Pharmacol. Exp. Ther. 212 (1980), 115–119) are used.

Since these substances, as σ a ligands, have a neuroprotective action, they are also suitable, in particular, as therapeutics for the treatment of stroke, for the treatment of cerebral and bone marrow traumata, and also for the treatment of ischaemic conditions after a cardiac arrest.

The compounds of the formula I are therefore suitable both in veterinary and in human medicine for the treatment of functional disorders of the central nervous system and of inflammations. They can be used for the prophylaxis and for the control of the sequelae of cerebral infarcts (cerebral apoplexia) such as stroke and cerebral ischaemias, and for the treatment of extrapyramidal motor side effects of neuroleptics and of Parksinson's disease, for the acute and symptomatic therapy of Alzheimer's disease and also for the treatment of amyotrophic lateral sclerosis. They are also suitable as therapeutics for the treatment of cerebral and bone marrow traumata. However, they are also suitable as pharmaceutical active compounds for axiolytics, antidepressants, antipsychotics, neuroleptics, antihypertensives and/or for positively affecting obsessive-compulsive disorder, sleep disorders, tardive dyskinesias, learning disorders, age-dependent memory disorders, eating disorders such as bulimia and/or sexual function disorders.

The invention thus relates to the compounds of the formula I and their physiologically acceptable acid addition salts.

The invention relates in particular to compounds of the formula I, selected from the group consisting of a) 3-[4-(3-benzylpiperidin-1-yl]butyl}indole;
b) 3-[4-(3-phenylhydroxyphenylpiperidin-1-yl)butyl]-indole
c) 3-[4-(3-benzylpiperidin-1-yl)butyl]-5-fluoro-indole;
d) 3-benzyl-1-[4-(5-fluoroindol-3-yl)butanoyl]-piperidine;
e) 3-benzyl-1-[4-(5-chloroindol-3-yl)butanoyl]-piperidine;
f) 3-[4-(3-benzylpiperidin-1-yl)butyl]-5-carboxy-indole;
g) methyl 3-[4-(3-benzylpiperidin-1-yl)butyl]indole-5-carboxylate;
h) methyl (−)-3-{4-[3-(3R')-benzylpiperidin-1-yl]-butyl}indole-5-carboxylate;
i) methyl (+)-3-{4-[3-(3S')-benzylpiperidin-1-yl]-butyl}indole-5-carboxylate;
j) 3-{4-[3-(3R')-benzylpiperidin-1-yl]butyl}-6-methoxyindole;
k) 3-{4-[3-(3S')-benzylpiperidin-1-yl]butyl}-6-methoxyindole;
l) (+)-3-[4-(3-benzylpiperidin-1-yl)butyl]indole;
m) (−)-3-[4-(3-benzylpiperidin-1-yl)butyl]indole;
n) 3-[4-(3-benzylpiperidin-1-yl)butyl]-5-chloro -indole;
o) 3-[4-(3-benzylpiperidin-1-yl)butyl]-5-methoxy -indole;
p) 3-{4-[3-(4-fluorobenzyl)piperidin-1-yl]butyl}-5-fluoroindole;
q) 7{4-[(3R)-3-benzylpiperidin-1-yl]butyl}-5H-1,3-dioxolo[4,5-f]indole;
r) 7{4-[(3S)-3-benzylpiperidin-1-yl]butyl}-5H-1,3-dioxolo[4,5-f]indole;
s) 3-{4-[(3R)-3-benzylpiperidin-1-yl]butyl}-5-fluoroindole;
t) 3-{4-[(3S)-3-benzylpiperidin-1-yl]butyl}-5fluoroindole;
u) 3-{4-[(3R)-3-benzylpiperidin-1-yl]butyl}indole-5-carbonitrile;
v) 3-{4-[(3S)-3-benzylpiperidin-1-yl]butyl}indole-5-carbonitrile;
w) 3-{4-[3-(4-fluorophenylhydroxymethyl)piperidin-1-yl]butyl}indole-5-carbonitrile;
and their salts and solvates.

The compounds (d), (e) and (f) are used as intermediates.

For all radicals which occur several times, such as, for example, A, it applies that their meanings are independent of one another.

The term solvates means for example the hemi- mono- or dihydrates or for example addition compounds with alcohols.

The radical A is alkyl and has 1 to 10, preferably 1, 2, 3, 4, 5 or 6, in particular 1 or 2, C atoms. Alkyl is therefore in particular, for example, methyl, furthermore ethyl, n-propyl, isopropyl, n-butyl, sec-butyl or tert-butyl, additionally also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methyl -propyl, 1-ethyl-2-methylpropyl, 1,1,2- or 1,2,2-tri-methylpropyl, additionally also fluoromethyl, difluoro-methyl, trifluoromethyl, 1,1,1-trichloroethyl or penta-fluoroethyl.

Cycloalkyl is in particular, for example, cyclopropyl, cyclobutyl, cyclopentyl, cyclohexyl, cycloheptyl or 1-adamantyl.

OA is preferably methoxy, additionally also ethoxy, n-propoxy, isopropoxy, n-butoxy, isobutoxy, sec-butoxy or tert-butoxy. NHA is preferably methylamino, additionally ethylamino, isopropylamino, n-butylamino, isobutylamino, sec-butylamino or tert-butylamino. $NA_2$ is preferably dimethylamino, additionally N-ethyl-N-methylamino, diethylamino, di-n-propyl-amino, diisopropylamino or di-n-butylamino. Resulting from this, CO—NHA is preferably N-methylcarbamoyl or N-ethylcarbamoyl; CO—$NA_2$ is preferably N,N-dimethyl-carbamoyl or N,N-diethylcarbamoyl.

Hal is fluorine, chlorine, bromine or iodine, in particular fluorine or chlorine. k is 0 or 1, preferably 0. If k is 1, intermediates for the synthesis of the actual active compounds are concerned. m is 1, 2, 3 or 4, in particular 3 or 4.

The radical $R^1$ is 2- or 3-indolyl which is preferably unsubstituted or mono- or disubstituted, but in particular monosubstituted, by Hal, CN, A, AO, OH, $CONH_2$, CONHA, $CONA_2$, COOH and/or COOA, additionally also 5H-1,3-dioxolo[4,5-f]-7-indolyl, which can likewise be unsubstituted, mono- or disubstituted, preferably by Hal, CN, A, AO or OH, in particular, however, this radical is present in unsubstituted form.

$R^1$ is therefore preferably 2- or 3-indolyl, 5- or 6-methylindol-2-yl, 5- or 6-methylindol-3-yl, 5- or 6-methoxyindol-2-yl, 5- or 6-methoxyindol-3-yl, 5- or 6-hydroxyindol-2-yl, 5- or 6-hydroxyindol-3-yl, 5- or 6-fluoroindol-2-yl, 5- or 6-fluoroindol-3-yl, 5- or 6-cyanoindol-2-yl, 5- or 6-cyanoindol-3-yl, 5- or 6-chloroindol-2-yl, 5- or 6-chloroindol-3-yl, 5- or 6-carboxyindol-2-yl, 5- or 6-carboxyindol-3-yl, 5- or 6-methoxycarbonylindol-2-yl, 5- or 6-methoxycarbonyl-indol-3-yl, 5H-1,3-dioxolo[4,5-f]indol-7-yl, additionally 5- or 6-bromoindol-2-yl, 5- or 6-bromoindol-3-yl, 5- or 6-ethylindol-2-yl, 5- or 6-ethylindol-3-yl, 5- or 6-trifluoromethylindol-2-yl, 5- or 6-trifluoromethyl-indol-3-yl, 5- or 6-isopropylindol-2-yl, 5- or 6-iso-propylindol-3-yl, 5- or 6-dimethylaminoindol-3-yl or 5- or 6-dimethylaminoindol-2-yl, 5- or 6-ethoxyindol-3-yl or 5- or 6-ethoxyindol-2-yl.

The radical $R^2$ is preferably benzyl or phenylhydroxymethyl which is unsubstituted or mono-, di- or trisubstituted by Hal, OH, OA, A, $NH_2$, NHA, $NA_2$, $CONH_2$, CONHA, $CONA_2$, COOH, COA, $CF_3$, CN, $OSC_2A$, $OSO_2CF3$ and/or $NO_2$. Accordingly, $R^2$ is particularly preferably benzyl, phenylhydroxymethyl or benzyl or phenyl-hydroxymethyl which is monosubstituted by Hal, i.e., for example, p-fluorobenzyl or p-fluorophenylhydroxy-methyl, p-methylbenzyl or p-methylphenylhydroxymethyl, p-chlorobenzyl or p-chlorophenylhydroxymethyl. Additionally preferably, $R^2$ is p-aminobenzyl, p-methyl-aminobenzyl, p-dimethylaminobenzyl, p-ethylaminobenzyl, p-cyanobenzyl, m-fluorobenzyl, m-methylbenzyl or m-methylphenylhydroxymethyl, p-nitrobenzyl or p-nitrophenylhydroxymethyl.

For the entire invention, it applies that all radicals which can occur several times in one molecule can be identical or different, i.e. are independent of one another.

Accordingly, the invention relates in particular to those compounds of the formula I in which at least one of the radicals mentioned has one of the preferred meanings indicated above. Some preferred groups of compounds can be expressed by the formulae Ia to Ik below, which correspond to the formula I and in which the radicals which are not designated in greater detail have the meaning indicated in the formula I, but in which in Ia $R^1$ is unsubstituted 3-indolyl;

in Ib $R^1$ is 3-indolyl substituted in the 5-position;

in Ic k is 0 and m is 4;

in Id k is 1 and m is 3;

in Ie $R^1$ has a meaning indicated in Ib and the substituent is Hal, methoxycarbonyl, CN or carboxyl;

in If $R^1$ is 5H-1,3-dioxolo[4,5-f]indol-7-yl;

in Ig $R^2$ is unsubstituted benzyl;

in Ih $R^2$ has a meaning indicated in Ig, but where the benzyl ring is present in monosubstituted form;

in Ii $R^2$ has a meaning indicated in Ih and the substituent is Hal;

in Ij $R^2$ is unsubstituted or monosubstituted phenyl-hydroxymethyl;

in Ik $R^2$ has a meaning indicated in Ij and the substituent is Hal.

The invention furthermore relates to a process for the preparation of compounds of the formula I and of their salts and solvates, characterized in that a compound of the formula II

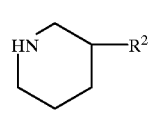

(II)

in which $R^2$ has the meaning indicated, is reacted with a compound of the formula III $$R^1-(CH_2)_m-(CO)_k-L \qquad (III)$$

in which

L is Cl, Br, I, OH, OCOA, OCOPh, $OSO_2A$, $OSO_2Ar$, where Ar is phenyl or tolyl and A is alkyl, or is another reactive esterified OH group or easily nucleophilically substitutable leaving group and $R^1$, m and k have the meanings indicated in the claims, or in a reductive amination a compound of the formula IV $$R^1-(CH_2)_{m-1}-CHO \qquad (IV)$$

in which $R^1$ and m have the meanings indicated in claim 1, is reacted with a compound of the formula II, or in that a compound otherwise corresponding to the formula I, but which instead of one or more hydrogen atoms contains one or more reducible group(s) such as C=O and/or one or more additional C—C— and/or C—N bond (s), is treated with a reducing agent, or in that a compound otherwise corresponding to the formula I, but which instead of one or more hydrogen atoms contains one or more solvolysable group(s), is treated with a solvolysing agent,
and/or in that a radical $R^1$ and/or $R^2$ is optionally converted into another radical $R^1$ and/or $R^2$ by cleaving, for example, an OA group with formation of an OH group and/or derivatizing a CN, COOH or COOA group and/or in that, for example, a primary or secondary N atom is alkylated and/or a base or acid of the formula I obtained is converted into one of its salts by treating with an acid or base.

The compounds of the formula I are otherwise prepared by methods known per se, such as are described in the literature (e.g. in standard works such as Houben-Weyl, Methoden der Organischen Chemie [Methods of Organic Chemistry], Georg Thieme Verlag, Stuttgart; Organic Reactions, John Wiley & Sons, Inc., New York; DE-A 41 01 686), namely under reaction conditions such as are known and suitable for the reactions mentioned. In this case, use can also be made of variants known per se, but not mentioned here in greater detail.

The starting substances for the claimed process can, if desired, also be formed in situ in such a way that they are not isolated from the reaction mixture, but immediately reacted further to give the compounds of the formula I.

The compounds of the formula I are preferably obtained by reacting compounds of the formula II with compounds of the formula III. As a rule, the starting substances of the formulae II and III are known; the unknown compounds of the formulae II and III can easily be prepared analogously to the known compounds.

The piperidine derivatives of the formula II are for the most part known. If they are not commercially available or known, they can be prepared by methods known per se.

The indole derivatives of the formula III are for the most part known and in some cases also commercially available. Furthermore, it is possible to prepare the compounds from known compounds by electrophilic or, in certain cases, also nucleophilic aromatic substitutions. The starting substance used is preferably an appropriate indole-3-alkanoic acid (which can be prepared analogously to a Japp-Klingemann type Fischer indole synthesis, cf., for this, Böttcher et al., J. Med. Chem. 1992, 35, 4020–4026 or Iyer et al., J. Chem. Soc. Perkin Trans. II 1973, 872–878). The acid group is then prepared for the reaction with the piperidine derivative by introduction of the reactive leaving group L, possibly after prior reduction of the acid group according to known methods, e.g. with lithium aluminium hydride in tetrahydrofuran, to the OH group.

The reaction of the compounds II and III proceeds according to methods such as are known from the literature for the alkylation or acylation of amines. The components can be fused with one another without the presence of a solvent, if appropriate in a closed tube or in an autoclave. However, it is also possible to react the compounds in the presence of an indifferent solvent. Suitable solvents are, for example, hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone (NMP); nitriles such as acetonitrile, and optionally also mixtures of these solvents with one another or mixtures with water. The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylaniline, pyridine or quinoline or of an excess of piperazine derivative of the formula I, may be favourable. The reaction time, depending on the conditions used, is between a few minutes and 14 days; the reaction temperature is between approximately 0 and 150°, normally between 20 and 130°.

It may be necessary, before carrying out this reaction, to protect other amino groups contained from alkylation or acylation by introduction of suitable protective groups. The expression amino protective group is generally known and relates to groups which are suitable for protecting an amino group from chemical reactions, but which are easily removable after the desired chemical reaction has been carried out at another position in the molecule. Since such protective groups and the introduction and removal of these are well known to the person skilled in the art from numerous literature references and textbooks, these do not have to be gone into in greater detail here.

Compounds of the formula I can furthermore be obtained by reductive amination of compounds of the formula IV using compounds of the formula II. The starting substances of the formulae IV and II are known in some cases. If they are not known, they can be prepared by methods known per se.

The reductive amination can be carried out in the presence of reducing agents such as, for example, $NaBH_3CN$ and $NaBH(OAc)_3$.

It is additionally possible to obtain a compound of the formula I by treating a precursor which, instead of hydrogen atoms, contains one or more reducible group(s) and/or one or more additional C—C and/or C—N bond(s), with a reducing agent, preferably at temperatures between −80 and +250° in the presence of at least one inert solvent.

Reducible (replaceable by hydrogen) groups are, in particular, oxygen in a carbonyl group, hydroxyl, arylsulfonyloxy (e.g. p-toluenesulfonyloxy), n-benzenesulfonyl, n-benzyl or o-benzyl.

It is fundamentally possible to convert compounds which only contain one group, or those which next to one another contain two or more of the abovementioned groups or additional bands, reductively to a compound of the formula I; in this case, substituents in the group I which are contained in the starting compound are simultaneously reduced. Preferably, nascent hydrogen or complex metal hydrides are used for this purpose, additionally Wolff-Kishner reduction, and reduction using hydrogen gas with transition metal catalysis.

If nascent hydrogen is used as the reducing agent, this can be produced, for example, by treatment of metals with weak acids or with bases. Thus, for example, a mixture of zinc with alkali metal hydroxide solution or of iron with acetic acid can be used. The use of sodium or another alkali metal dissolved in an alcohol such as ethanol, isopropanol, butanol, amyl or isoamyl alcohol or phenol is also suitable. An aluminium-nickel alloy in alkaline-aqueous solution, if appropriate with addition of ethanol, can additionally be used. Sodium or aluminium amalgam in aqueous-alcoholic or aqueous solution is also suitable for the generation of the nascent hydrogen. The reaction can also be carried out in a heterogeneous phase, an aqueous and a benzene or toluene phase expediently being used.

Reducing agents which can additionally be employed are particularly advantageously complex metal hydrides, such as $LiAlH_4$, $NaBH_4$, diisobutylaluminium hydride or $NaAl(OCH_2CH_2OCH_3)_2H_2$ and also diborane, if desired with addition of catalysts such as $BF_3$, $AlCl_3$ or LiBr. Suitable solvents for this purpose are in particular ethers such as diethyl ether, di-n-butyl ether, THF, dioxane, diglyme or 1,2-dimethoxyethane as well as hydrocarbons such as benzene. For reduction with $NaBH_4$, first and foremost alcohols such as methanol or ethanol, and additionally water as well as aqueous alcohols, are suitable as solvents. According to these methods, the reduction is preferably carried out at temperatures between −80 and +150°, in particular between approximately 0 and approximately 100°.

It is particularly advantageously possible to reduce —CO groups in acid amides to $CH_2$ groups using $LiAlH_4$ in THF at temperatures between approximately 0 and 66°.

It is additionally possible to reduce one or more carbonyl groups to $CH_2$ groups according to the Wolff-Kishner method, e.g. by treatment with anhydrous hydrazine in absolute ethanol under pressure and at temperatures between approximately 150 and 250°. The catalyst used is advantageously sodium alcoholate. The reduction can also be varied according to the Huang-Minlon method, by reacting with hydrazine hydrate in a high-boiling, water-miscible solvent such as diethylene glycol or triethylene glycol, in the presence of alkali, such as sodium hydroxide. As a rule, the reaction mixture is boiled for approximately 3–4 hours.

The water is then distilled off and the hydrazone formed is decomposed at temperatures up to approximately 200°. The Wolff-Kishner reduction can also be carried out at room temperature in dimethyl sulfoxide using hydrazine.

It is moreover possible to carry out certain reductions by use of $H_2$ gas with catalytic action of transition metals, such as, for example, Raney Ni or Pd. It is also possible in this manner, for example, to replace Cl, Br, I, SH or, in certain cases, also OH groups by hydrogen. Likewise, nitro groups can be converted into $NH_2$ groups by catalytic hydrogenation with $Pd/H_2$ in methanol.

Compounds which otherwise correspond to the formula I, but instead of one or more H atoms contain one or more solvolysable group(s), can be solvolysed, in particular hydrolysed, to give the compounds of the formula I.

It is furthermore possible to convert a compound of the formula I into another compound of the formula I by methods known per se.

Compounds of the formula I in which $R^1$ is a radical substituted by $CONH_2$, CONHA or $CONA_2$ can be obtained by derivatization of corresponding substituted compounds of the formula I by partial hydrolysis. It is additionally possible first to hydrolyse cyano-substituted compounds of the formula I to acids and to amidate the acids with primary or secondary amines. The reaction of the free carboxylic acid with the amine under the conditions of a peptide synthesis is preferred. This reaction preferably takes place in the presence of a dehydrating agent, e.g. of a carbodiimide such as dicyclohexylcarbodiimide or N-(3-dimethylaminopropyl)-N-ethylcarbodiimide, additionally propanephosphonic anhydride (cf. Angew. Chem. 92, 129 (1980)), diphenylphosphoryl azide or 2-ethoxy-N-ethoxycarbonyl -1,2-dihydroquinoline, in an inert solvent, e.g. a halogenated hydrocarbon such as dichloromethane, an ether such as THF or dioxane, an amide such as DMF or dimethylacetamide, a nitrile such as acetonitrile, at temperatures between approximately −10 and 40°, preferably between 0 and 30°.

However, it is also particularly convenient to prepare the nitrites in the reverse manner, by elimination of water, starting from the amides, e.g. by means of trichloroacetyl chloride/$Et_3N$ [Synthesis (2), 184 (1985)] or with $POCl_3$ (J. Org. Chem. 26, 1003 (1961)).

A base of the formula I obtained can be converted into the associated acid addition salt using an acid. Acids suitable for this reaction are those which yield physiologically acceptable salts. Thus it is possible to use inorganic acids, e.g. sulfuric acid, hydrohalic acids such as hydrochloric acid or hydrobromic acid, phosphoric acids such as orthophosphoric acid, nitric acid, sulfamic acid, additionally organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid.

If desired, the free bases of the formula I can be set free from their salts by treatment with strong bases such as sodium hydroxide or potassium hydroxide, sodium carbonate or potassium carbonate, if no further acidic groups are present in the molecule.

In those cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

Compounds of the formula I according to the invention can be chiral as a result of their molecular structure and can accordingly occur in two enantiomeric or a number of diastereomeric forms. As a result of one or more chiral centres, they can therefore be present in racemic or in optically active form.

Since the pharmaceutical activity of the racemates or of the stereoisomers of the compounds according to the invention can differ, it may be desirable to use the diastereomers or enantiomers. In these cases, the final product or else even the intermediates can be resolved into enantiomeric compounds, by chemical or physical measures known to the person skilled in the art, or even employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids or the various optically active camphorsulfonic acids. Also advantageous is a chromatographic enantiomer separation with the aid of an optically active resolving agent (e.g. dinitrobenzoylphenylglycine, cellulose triacetate or other derivatives of carbohydrates or chirally derivatized methacrylate polymers attached to silica gel). Suitable eluents for this purpose are aqueous or alcoholic solvent mixtures.

In the case of racemic acids, it is analogously possible to use optically active bases, such as, for example, the R and S form of 1-phenylethylamine, 1-naphthylethylamine, dihydroabietylamine, cinchonine or cinchonidine.

Under particular conditions, however, it is also possible even during the synthesis to employ corresponding enantiomerically pure intermediates which have been prepared by one of the abovementioned processes. In this case, the chirality in the course of the further synthesis is retained.

The invention additionally relates to the use of the compounds of the formula I and their physiologically acceptable salts for the production of pharmaceutical preparations, in particular by a non-chemical route. In this context, they can be brought into a suitable dose form together with at least one solid, liquid and/or semi-liquid excipient or auxiliary and, if appropriate, in combination with one or more other active compound(s).

The invention additionally relates to compositions, in particular pharmaceutical preparations, comprising at least one compound of the formula I and/or one of its physiologically acceptable salts. These preparations can be employed as pharmaceuticals in human and veterinary medicine. Possible excipients are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc, petroleum jelly. Tablets, coated tablets, capsules, syrups, juices, drops or suppositories are in particular used for enteral administration, solutions, preferably oily or aqueous solutions, and also suspensions, emulsions or implants for parenteral administration, and ointments, creams or powders for topical application. The novel compounds can also be lyophilized and the lyophilizates obtained used, for example, for the production of injection preparations.

The preparations indicated can be sterilized and/or can contain auxiliaries such as lubricants, preservatives, stabilizers and/or wetting agents, emulsifiers, salts for affecting the osmotic pressure, buffer substances, colorants, flavourings and/or aromatic substances. If desired, they can also contain one or more further active compounds, e.g. one or more vitamins.

The compounds of the formula I and their physiologically acceptable salts can be used in the therapeutic treatment of the human or animal body and in the control of diseases.

They are suitable for the treatment of disorders of the central nervous system such as tension states, depression, anxiety states, schizophrenia, gastrointestinal tract disorders, nausea, tardive dyskinesia, Parkinsonism and/or psychoses and of side effects in the treatment of hypertension (e.g. with α-methyldopa). The compounds can also be used in endocrinology and gynaecology, e.g. for the therapy of acromegaly, hypogonadism, secondary amenorrhoea, premenstrual syndrome, undesired puerperal lactation, and furthermore for the prophylaxis and therapy of cerebral disorders (e.g. migraines), in particular in geriatrics, similarly to certain ergot alkaloids.

Particularly preferably, they can also be employed as therapeutics for the control of the sequelae of cerebral infarcts (cerebral apoplexy), such as stroke and cerebral ischaemias, and for the treatment of cerebral and bone marrow traumata.

In this case, the substances according to the invention are as a rule administered in analogy to similarly acting known preparations, preferably in doses between approximately 0.1 and 500 mg, in particular between 0.2 and 300 mg per dose unit. The daily dose is preferably between approximately 0.001 and 250 mg/kg of body weight.

The specific dose for each specific patient depends, however, on all sorts of factors, for example on the activity of the specific compound employed, on the age, body weight, general state of health, sex, on the diet, on the time and route of administration, on the excretion rate, pharmaceutical combination and severity of the particular disorder to which the therapy relates. Oral administration is preferred.

Above and below, all temperatures are indicated in ° C. In the examples below, "customary working up" means: water is added, if necessary, the mixture is adjusted, if necessary, depending on the constitution of the final product, to a pH of between 2 and 10, and extracted with ethyl acetate or dichloromethane, the organic phase is separated off, dried over sodium sulfate, filtered and evaporated and the residue is purified by chromatography on silica gel, a separation of the isomers described below also taking place, and/or by crystallization. $R_f$ values were obtained by thin-layer chromatography on silica gel. $(M+1)^+$ values were determined by FAB-MS (Fast Atom Bombardment Mass Spectroscopy). The specific rotations of the optically active compounds indicated were in each case measured on solutions of the free bases.

EXAMPLE 1 a) A solution of 4-(5-fluoroindol-3-yl)butanoic acid [obtainable, for example, by diazotization of the appropriately substituted aniline, condensation of the diazonium salt with ethyl 1-oxocyclohexane-2-carboxylate by the Japp-Klingemann method to give the corresponding 4-(5-fluoro-2-ethoxycarbonylindol-3-yl)butanoic acid and subsequent hydrolysis and decarboxylation of the ethoxycarbonyl group] in THF is subjected to reduction using lithium aluminium hydride. After customary working up 4-(5-fluoroindol-3-yl)butanol is obtained.

This is converted by reaction with methanesulfonyl chloride into the reactive 4-(5-fluoroindol-3-yl)-butyl methanesulfonate.

b) A mixture of 2.80 g (0.0098 mol) of 4-(5-fluoroindol-3-yl)butyl methanesulfonate, 3.20 g (0.0097 mol) of (S)-(+)-mandelic acid/3-benzylpiperidine) and 3.80 g (0.0294 mol) of ethyldiisopropylamine is heated on a steam bath for about 96 hours in 100 ml of acetonitrile. The reaction mixture is then filtered and concentrated, and the residue is dissolved in ethyl acetate and extracted with water. The organic phase is worked up, and the residue is chromatographed on a silica gel column in ethyl acetate. The fractions were concentrated, the residue was dissolved in ethyl acetate and using ethanolic HCl the hydrochloride of 3-{4-[(3S)-3-benzylpiperidin-1-yl]butyl}-5-fluoroindole was precipitated and worked up, m.p. 152.0–153.0° C., $\alpha^{D20}$ (+) 9.7° (c 1.0, dimethyl sulfoxide).

Analogously, by reaction of 4-(5-fluoroindol-3-yl)butyl methanesulfonate with (R)-(–)-(3-benzylpiperidine) mandelate the corresponding hydrochloride of 3-{4-[(3R)-3-benzylpiperidin-1-yl]butyl}-5-fluoroindole of m.p. 153.0–154.0°, $\alpha_D^{20}$ (–) 10.80 (c 1.0, dimethyl sulfoxide) is obtained.

The following are obtained analogously:

(+)-3-[4-(3-benzylpiperidin-1-yl)butyl]indole, m.p. 74–75°, ($\alpha^{20}$ (+) 22.1°(c 1.0, dimethyl sulfoxide);

(–)-3-[4-(3-benzylpiperidin-1-yl)butyl]indole, m.p. 73–74°, $\alpha_D^{20}$ (–) 22.8° (c 1.0, dimethyl sulfoxide);

methyl (+)-3-{4-[3-(3S')-benzylpiperidin-1-yl]butyl}-indole-5-carboxylate; $\alpha_D^{20}$ (+) 6.0° (c 1.0, dimethyl sulfoxide);

methyl (–)-3-{4-[3-(3R')-benzylpiperidin-1-yl]butyl}-indole-5-carboxylate; $\alpha_D^{20}$ (–) 8.1° (c 1.0, dimethyl sulfoxide);

3-{4-[(3R')-3-benzylpiperidin-1-yl]butyl}-6-methoxy-indole, hydrochloride, m.p. 218–221°, $\alpha_D^{20}$ (–) 7.3° (c 1.0, dimethyl sulfoxide);

3-{4-[(3S')-3-benzylpiperidin-1-yl]butyl}-6-methoxy-indole, hydrochloride, m.p. 217–220°, $\alpha_D^{20}$ (+) 7.5° (c 1.0, dimethyl sulfoxide).

EXAMPLE 2

Analogously to Example 1a) and b), but without adding the mandelic acid in step b), starting from 4-(5-fluoroindol- 3-yl)butanoic acid via 4-(5-fluoroindol-3-yl)butyl methanesulfonate by reaction with 3-benzylpiperidine, 3-[4-(3-benzylpiperidin-1-yl)-butyl]-5-fluoroindole, hydrochloride, m.p. 163–165°, is obtained.

Analogously, by reaction of
4-(indol-3-yl)butyl methanesulfonate with 3-benzylpiperidine, 3-[4-(3-benzylpiperidin-1-yl)butyl] indole, hydrochloride, m.p. 134–136°;
4-(5-chloroindol-3-yl)butyl methanesulfonate with 3-benzylpiperidine, 3-[4-(3-benzylpiperidin-1-yl)-butyl]-5-chloroindole, malonate, m.p. 127–129°;
4-(5-fluoroindol-3-yl)butyl methanesulfonate with 3-(4-fluorobenzyl)piperidine, 3-{4-[3-(4-fluorobenzyl)-piperidin-1-yl]butyl}-5-fluoroindole are obtained.

EXAMPLE 3

A solution of equivalent amounts of 3-benzylpiperidine and 3-(4-chlorobutyl)-5-cyanoindole (obtainable, for example, by halogenation of the corresponding alcohol compound, which can be prepared analogously to Example 1a) by reduction of 4-(5-cyanoindol-3-yl)butanoic acid) in acetonitrile is stirred at room temperature for about 6 hours. After customary work-up and resolution of the chiral compounds, 3-{4 -[(3S)-3-benzylpiperidin-3-yl]butyl}-5-cyanoindole, $\alpha_D^{20}$ (+)8.9° (c 1.0, dimethyl sulfoxide), is obtained as the hydrochloride, m.p. 65–67° (amorphous); or the corresponding 3-{4-[(3R)-3-benzylpiperidin-3-yl]-butyl}-5-cyanoindole, $\alpha_D^{20}$ (−) 10.4° (c 1.0, dimethyl sulfoxide), is obtained as the hydrochloride, m.p. 65–75° (amorphous).

The following can be prepared analogously:
7-{4-[(3R)-3-benzylpiperidin-1-yl]butyl}-5H-1,3-dioxolo [4,5-f]indole, $R_f$ 0.4 (in $CHCl_3$:MeOH 95:5);
7-{4-[(3S)-3-benzylpiperidin-1-yl]butyl}-5H-1,3-dioxolo [4,5-f]indole, $R_f$ 0.4 (in $CHCl_3$:MeOH 95:5).

EXAMPLE 4

Equimolar amounts of 3-benzylpiperidine and 4-(5-methoxyindol-3-yl)butanoic acid (preparation analogous to Example 1a) are reacted at room temperature with addition of 2-chloro-1-methyl-pyridinium iodide. After customary work-up, 3-benzyl-1-[4-(5-methoxyindol-3-yl)butanoyl] piperidine is obtained.

The following are prepared analogously:
3-benzyl-1-[4-(5-fluoroindol-3-yl)butanoyl]piperidine;
3-benzyl-1-[4-(5-chloroindol-3-yl)butanoyl]piperidine;
3-benzyl-1-[4-(5-chloroindol-3-yl)butanoyl]piperidine;
3-benzyl-1-[4-(6-fluoroindol-3-yl)butanoyl]piperidine;
3-benzyl-1-[4-(6-methoxyindol-3-yl)butanoyl]piperidine;
3-benzyl-1-[4-(6-ethoxyindol-3-yl)butanoyl]piperidine;
3-benzyl-1-[4-(6-ethoxyindol-3-yl)butanoyl]piperidine;
3-benzyl-1-[4-(5-cyanoindol-3-yl)butanoyl]piperidine;
3-benzyl-1-[4-(6-cyanoindol-3-yl)butanoyl]piperidine;
3-benzyl-1-[4-(5-fluoroindol-2-yl)butanoyl]piperidine;
3-benzyl-1-[4-(5-chloroindol-2-yl)butanoyl]piperidine;
3-benzyl-1-[4-(6-chloroindol-2-yl)butanoyl]piperidine;
3-benzyl-1-[4-(6-fluoroindol-2-yl)butanoyl]piperidine;
3-benzyl-1-[4-(6-methoxyindol-2-yl)butanoyl]piperidine;
3-benzyl-1-[4-(6-ethoxyindol-2-yl)butanoyl]piperidine;
3-benzyl-1-[4-(5-ethoxyindol-2-yl)butanoyl]piperidine;
3-benzyl-1-[4-(5-cyanoindol-2-yl)butanoyl]piperidine;
3-benzyl-1-[4-(6-cyanoindol-3-yl)butanoyl]piperidine.

EXAMPLE 5

3-benzyl-1-[4-(5-methoxyindol-3-yl)butanoyl]-piperidine is reacted with lithium aluminium hydride in THF. After customary work-up, 3-[4-(3-benzylpiperidin-1-yl)butyl]-5-methoxyindole, hydrochloride, m.p. 222–224°, is obtained.

The following can be prepared analogously:
3-[4-(3-benzylpiperidin-1-yl)butyl]-5-fluoroindole;
3-[4-(3-benzylpiperidin-1-yl)butyl]-5-chloroindole;
3-[4-(3-benzylpiperidin-1-yl)butyl]-6-chloroindole;
3-[4-(3-benzylpiperidin-1-yl)butyl]-6-fluoroindole;
3-[4-(3-benzylpiperidin-1-yl)butyl]-6-methoxyindole;
3-[4-(3-benzylpiperidin-1-yl)butyl]-6-ethoxyindole;
3-[4-(3-benzylpiperidin-1-yl)butyl]-5-ethoxyindole;
3-[4-(3-benzylpiperidin-1-yl)butyl]-5-cyanoindole;
3-[4-(3-benzylpiperidin-1-yl)butyl]-6-cyanoindole;
2-[4-(3-benzylpiperidin-1-yl)butyl]-5-fluoroindole;
2-[4-(3-benzylpiperidin-1-yl)butyl]-5-chloroindole;
2-[4-(3-benzylpiperidin-1-yl)butyl]-6-chloroindole;
2-[4-(3-benzylpiperidin-1-yl)butyl]-6-fluoroindole;
2-[4-(3-benzylpiperidin-1-yl)butyl]-6-methoxyindole;
2-[4-(3-benzylpiperidin-1-yl)butyl]-6-ethoxyindole;
2-[4-(3-benzylpiperidin-1-yl)butyl]-5-ethoxyindole;
2-[4-(3-benzylpiperidin-1-yl)butyl]-5-cyanoindole;
2-[4-(3-benzylpiperidin-1-yl)butyl]-6-cyanoindole.

EXAMPLE 6

3-[4-(3-benzoylpiperidin-1-yl)butyl]indole is subjected to a reduction by reaction with sodium borohydride in THF. After customary work-up, 3-[4-(3-phenylhydroxymethylpiperidin-1-yl)butyl]indole, hydrochloride, m.p. 181–183°, is obtained.

The following are prepared analogously:
3-[4-(3-phenylhydroxymethylpiperidin-1-yl)butyl]-5-fluoroindole;
3-{4-[3-(3R')phenylhydroxymethylpiperidin-1-yl]butyl}-6-methoxyindole;
3-{4-[3-(3S')phenylhydroxymethylpiperidin-1-yl]butyl}-6-methoxyindole;
3-[4-(3-phenylhydroxymethylpiperidin-1-yl)butyl]-5-chloroindole;
3-[4-(3-phenylhydroxymethylpiperidin-1-yl)butyl}-5-methoxyindole;
3-{4-[3-(4-fluorophenylhydroxymethyl)piperidin-1-yl] butyl}-5-fluoroindole;
3-{4-[(3R)-3-phenylhydroxymethylpiperidin-1-yl]butyl}-5-fluoroindole;
3-{4-[(3S)-3-phenylhydroxymethylpiperidin-1-yl]butyl}-5-fluoroindole;
3-{4-[(3R)-3-phenylhydroxymethylpiperidin-1-yl]butyl}-indole-5-carbonitrile;
3-{4-[(3S)-3-phenylhydroxymethylpiperidin-1-yl]butyl}-indole-5-carbonitrile;
3-{4-[3-(4-fluorophenylhydroxymethyl)piperidin-1-yl]-butyl}indole-5-carbonitrile, m.p. 157–159°.

EXAMPLE 7

A mixture of 0.0098 mol of 4-(5-methoxycarbonylindol-3-yl)butyl methanesulfonate (preparation analogous to Example 1a) and 0.0097 mol of 3-benzylpiperidine is heated on a steam bath analogously to Example 1b in acetonitrile for about 96 hours. The reaction mixture is worked up and purified as described. Methyl 3-[4-(3-benzylpiperidin-1-yl) butyl]-indole-5-carboxylate, hydrochloride, m.p. 181–183°, is thus obtained.

The following can be prepared analogously:
methyl 3-{4-[3-(4-fluorobenzyl)piperidin-1-yl]butyl}-indole-5-carboxylate;
methyl 3-{4-[3-(4-cyanobenzyl)piperidin-1-yl]butyl}-indole-5-carboxylate;

methyl 3-{4-[3-(4-ethylbenzyl)piperidin-1-yl]butyl}-indole-5-carboxylate;
methyl 3-{4-[3-(4-methylbenzyl)piperidin-1-yl]butyl}-indole-5-carboxylate;
methyl 3-{4-[3-(4-methoxybenzyl)piperidin-1-yl]butyl}-indole-5-carboxylate;
methyl 3-{4-[3-(4-fluorobenzyl)piperidin-1-yl]butyl}-indole-6-carboxylate;
methyl 3-{4-[3-(4-fluorobenzyl)piperidin-1-yl]butyl}-indole-5-carboxylate;
methyl 3-[4-(3-benzylpiperidin-1-yl)butyl]indole-6-carboxylate;
methyl 3-{4-[3-(4-cyanobenzyl)piperidin-1-yl]butyl}-indole-6-carboxylate;
methyl 3-{4-[3-(4-methylbenzyl)piperidin-1-yl]butyl}-indole-6-carboxylate.

EXAMPLE 8

A mixture of methyl 3-[4-(3-benzylpiperidin-1-yl)butyl] indole-5-carboxylate and KOH is heated under reflux in ethanol. After customary work-up, 3-[4-(3-benzylpiperidin-1-yl)butyl]-5-carboxyindole, hydrate, m.p. 144–147°, is obtained.

The following examples relate to pharmaceutical preparations:

EXAMPLE A

Injection Vials

A solution of 100 g of an active compound of the formula I and 5 g of disodium hydrogenphosphate in 3 l of double-distilled water is adjusted to pH 6.5 using 2 N hydrochloric acid, sterile-filtered, dispensed into injection vials, lyophilized and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and left to cool. Each suppository contains 20 mg of active compound.

EXAMPLE C

Solution

A solution of 1 g of an active compound of the formula I, 9.38 g of $NaH_2PO_4 \times 2\ H_2O$, 28.48 g of $NaH_2PO_4 \times 12\ H_2O$ and 0.1 g of benzalkonium chloride in 940 ml of double-distilled water is prepared. It is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE F

Coated Tablets

Analogously to Example E, tablets are pressed which are then coated in a customary manner with a coating of sucrose, potato starch, talc, tragacanth and colorant.

EXAMPLE G

Capsules 2 kg of active compound of the formula I are dispensed into hard gelatin capsules in a customary manner, such that each capsule contains 20 mg of the active compound.

EXAMPLE H

Ampoules

A solution of 1 kg of active compound of the formula I in 60 l of double-distilled water is dispensed into ampoules, lyophilized under aseptic conditions and sealed aseptically. Each ampoule contains 10 mg of active compound.

What is claimed is:

1. A compound of the formula I

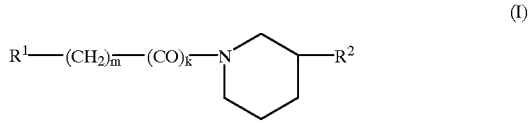

(I)

in which
$R^1$ is 2- or 3-indolyl which is unsubstituted or mono- or disubstituted by Hal, CN, A, AO, OH, $CONH_2$, CONHA, $CONA_2$, COOH and/or COOA, or is 5H-1,3-dioxolo-[4,5-f]-7-indolyl, $R^2$ is benzyl which is unsubstituted or mono-, di- or trisubstituted on the phenyl ring by A, AO, OH, Hal, CN, $NO_2$, $NH_2$, NHA, $NA_2$, $CF_3$, COA, $CONH_2$, COOH, CONHA, $CONA_2$, $OSO_2A$ and/or $OSO_2CF_3$ or is phenylhydroxymethyl, Hal is F, Cl, Br or I, A is straight-chain or branched alkyl having 1–10 C atoms, which can be substituted by 1 to 5 F and/or Cl atoms or is cycloalkyl having 3–10 C atoms, k is 0 or 1 and m is 1, 2, 3 or 4 and their salts and solvates.

2. A stereoisomer of the compound of formula I according to claim 1.

3. A compound according to claim 1, wherein the compound is selected from,
a) 3-[4-(3-benzylpiperidin-1-yl]butyl}indole;
b) 3-[4-(3-phenylhydroxymethylpiperidin-1-yl)butyl]-indole;
c) 3-[4-(3-benzylpiperidin-1-yl)butyl]-5-fluoro-indole;
d) 3-benzyl-1-[4-(5-fluoroindol-3-yl)butanoyl]-piperidine;
e) 3-benzyl-1-[4-(5-chloroindol-3-yl)butanoyl]-piperidine;
f) 3-[4-(3-benzylpiperidin-1-yl)butyl]-5-carboxy-indole;
g) methyl 3-[4-(3-benzylpiperidin-1-yl)butyl]indole-5-carboxylate;
h) methyl (−)-3-{4-[3-(3R')-benzylpiperidin-1-yl]-butyl}indole-5-carboxylate;
i) methyl (+)-3-{4-[3-(3S')-benzylpiperidin-1-yl]-butyl}indole-5-carboxylate;
j) 3-{4-[3-(3R')-benzylpiperidin-1-yl]butyl}-6-methoxyindole;
k) 3-{4-[3-(3S')-benzylpiperidin-1-yl]butyl}-6-methoxyindole;
l) (+)-3-[4-(3-benzylpiperidin-1-yl)butyl]indole;
m) (−)-3-[4-(3-benzylpiperidin-1-yl)butyl]indole;
n) 3-[4-(3-benzylpiperidin-1-yl)butyl]-5-chloroindole;
o) 3-[4-(3-benzylpiperidin-1-yl)butyl]-5-methoxy-indole;
p) 3-{4-[3-(4-fluorobenzyl)piperidin-1-yl]butyl}-5-fluoroindole;
q) 7{4-[(3R)-3-benzylpiperidin-1-yl]butyl}-5H-1,3-dioxolo[4,5-f]indole;

r) 7{4-[(3S)-3-benzylpiperidin-1-yl]butyl}-5H-1,3-dioxolo[4,5-f]indole;
s) 3-{4-[(3R)-3-benzylpiperidin-1-yl]butyl}-5-fluoro-indole;
t) 3-{4-[(3S)-3-benzylpiperidin-1-yl]butyl}-5-fluoro-indole;
u) 3-{4-[(3R)-3-benzylpiperidin-1-yl]butyl}indole-5-carbonitrile;
v) 3-{4-[(3S)-3-benzylpiperidin-1-yl]butyl}indole-5-carbonitrile;
w) 3-{4-[3-(4-fluorophenylhydroxymethol)piperidin-1-yl]butyl}indole-5-carbonitrile;
and their salts.

4. A process for the preparation of compounds of the formula I according to claim 1, wherein a compound of the formula II

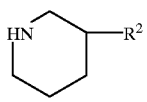

(II)

in which $R^2$ has the meaning indicated in claim 1, is reacted with a compound of the formula III

$R^1$—$(CH_2)_m$—$(CO)_k$—L (III)

in which

L is Cl, Br, I, OH, OCOA, OCOPh, $OSO_2A$, $OSO_2Ar$, where Ar is phenyl or tolyl and A is alkyl, or another reactive esterified OH group or easily nucleophilically substitutable leaving group and $R^1$, m and k have the meanings indicated in claim 1, or in a reductive amination a compound of the formula IV

$R^1$—$(CH_2)_{m-1}$—CHO (IV)

in which R' and m have the meanings indicated in claim 1, is reacted with a compound of the formula II,
or in that a compound otherwise corresponding to the formula I, but which instead of one or more hydrogen atoms contains one or more reducible group(s) and/or one or more additional C—C— and/or C—N bond(s), is treated with a reducing agent,
or in that a compound otherwise corresponding to the formula I, but which instead of one or more hydrogen atoms contains one or more solvolysable group(s), is treated with a solvolysing agent,
and/or in that a radical $R^1$ and/or $R^2$ is optionally converted into another radical $R^1$ and/or $R^2$ be cleaving, and/or derivatizing a CN, COOH, COOA group and/or in that, for example, a primary or secondary N atom is alkylated and/or a base or acid of the formula I obtained is converted into one of its salts by treating with an acid or base.

5. A process for the production of a pharmaceutical preparation, comprising combining a therapeutic amount of a compound according to claim 1, and at least one solid, liquid or semi-liquid excipient or auxiliary and, optionally, one or more other active compounds.

6. A pharmaceutical preparation, comprising a therapeutic amount of at least one compound according to claim 1, and at least one solid, liquid or semi-liquid excipient or auxiliary and, optionally, one or more other active compounds.

7. A compound according to claim 1, wherein $R^1$ is 2- or 3-indolyl, 5- or 6-methylindol-2-yl, 5- or 6-methylindol-3-yl, 5- or 6-methoxyindol 2-yl, 5- or 6-methoxyindol-3-yl, 5- or 6-fluoroindol-2-yl, 5- or 6-fluoroindol-3-yl, 5- or 6-cyanoindol-2-yl, 5- or 6-cyanoindol-3 yl, 5- or 6 chloroindol-2-yl, 5- or 6-chloroindol-3-yl, 5- or 6-carboxyindol-2-yl, 5- or 6-carboxyindol-3-yl, 5- or 6-methoxycarboxyindol-2-yl, 5- or 6-methoxycarboxyindol-3-yl, 5H-1,3 dioxolo[4,5-f] indol-7-yl, 5- or 6-bromoindol-2-yl, 5- or 6-bromoindol-3-yl, 5- or 6-ethylindol-2-yl, 5- or 6-ethylindol-3-yl, 5- or 6 trifluoromethylindol-2-yl, 5- or 6-trifluoromethylindol-3-yl, 5- or 6-isopropyloindol-2-yl, 5- or 6-isopropylindol 3-yl, 5- or 6-dimethylaminoindol-2-yl, 5- or 6-dimethylaminoindol-3-yl, 5- or 6-ethoxyindol-2yl, or 5- or 6-ethoxyindol-3-yl.

8. The compounds according to claim 1, wherein $R^2$ is benzyl, phenylhydroxymethyl or benzyl or phenyl-hydroxymethyl which monosubstituted by a halogen.

9. The compounds according to claim 8, wherein $R^2$ is p-fluorobenzyl, p fluorophenylhydroxymethyl, p-methylbenzyl, p-methylphenylhydroxymethyl, p-methylbenzyl, p-methylphenylhydroxymethyl, p-chlorobenzyl, or p-chlorophenylhydroxymethyl.

10. The compounds according to claim 8, wherein $R^2$ is p-aminobenzyl, p-methylaminobenzyl, p-dimethylaminobenzyl, p-ethylaminobenzyl, p-cyanobenzyl, m-fluorobenzyl, m-methylbenzyl , p-methylphenylhydroxymethyl, p-nirrobenzyl, or p-nitrophenylhydroxymethyl.

11. A method of treating a patient suffering from schizophrenia, cognitive defects, anxiety, depression, nausea, tardive dyskinesia, gastrointestinal tract disorders or Parkinsonism comprising administering to said patient an effective amount of a compound according to claim 1.

12. A method for the treatment of strokes, cerebral and bone marrow trauma or cerebral ischaemias comprising administering to said patient an effective amount of a compound according to claim 1.

13. A method for the treatment of acromegaly, hypdgonadism, secondary amenorrhea, premenstrual syndrome, undesired puerperal lactation comprising administering to said patient an effective amount of a compound according to claim 1.

14. A method for the treatment of migraines comprising administering to a patient an effective amount of a compound according to claim 1.

* * * * *

UNITED STATES PATENT AND TRADEMARK OFFICE
CERTIFICATE OF CORRECTION

PATENT NO. : 6,333,339 B1  Page 1 of 1
DATED : December 25, 2001
INVENTOR(S) : Boettcher et al.

It is certified that error appears in the above-identified patent and that said Letters Patent is hereby corrected as shown below:

Title page,
Item [57], ABSTRACT, first line of second paragraph, delete "a" and insert -- $\sigma$ --.

Column 16,
Line 36, delete "p-nirrobenzyl" and insert -- p-nitrobenzyl --.

Signed and Sealed this

Thirty-first Day of December, 2002

JAMES E. ROGAN
*Director of the United States Patent and Trademark Office*